United States Patent [19]

Baker et al.

[11] 4,081,441
[45] Mar. 28, 1978

[54] ANTIBACTERIAL AGENTS

[75] Inventors: Stephen Richard Baker, Cicero; Charles Truman Holdrege, Camillus, both of N.Y.

[73] Assignee: Bristol-Myers Company, New York, N.Y.

[21] Appl. No.: 785,280

[22] Filed: Apr. 6, 1977

Related U.S. Application Data

[63] Continuation-in-part of Ser. No. 730,091, Oct. 6, 1976, abandoned.

[51] Int. Cl.² ............................................ C07D 499/68
[52] U.S. Cl. .................................. 260/239.1; 424/271
[58] Field of Search ...................................... 260/239.1

[56] References Cited
U.S. PATENT DOCUMENTS

3,945,995   3/1976   Yamada et al. .................. 260/239.1

Primary Examiner—Gerald A. Schwartz

Attorney, Agent, or Firm—David M. Morse

[57] ABSTRACT

The penicillanic acids of the formula

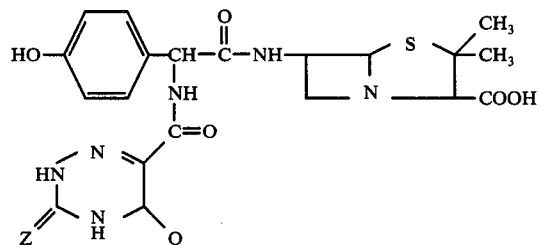

wherein Z is an oxygen or sulfur atom and their pharmaceutically acceptable salts and physiologically hydrolyzed esters possess antibacterial activity and are particularly valuable in treating Pseudomonas infections.

23 Claims, 2 Drawing Figures

FIG. I
SYNERGISTIC BACTERICIDAL EFFECT OF
AMIKACIN SULFATE AND BL-P1908
AGAINST P. AERUGINOSA A9843 A

FIG. 2
PROTECTIVE ACTIVITY (mg/kg/TREATMENT) OF IM-ADMINISTERED BL-P1908 (P), AMIKACIN (A), AND P/A COMBINATION FOR MICE INFECTED WITH PSEUDOMONAS AERUGINOSA A9843

ANTIBACTERIAL AGENTS

CROSS-REFERENCE TO RELATED APPLICATION

This application is a continuation-in-part of co-pending application Ser. No. 730,091 filed Oct. 6, 1976 now abandoned.

BACKGROUND OF THE INVENTION

1. Field of the Invention

The novel semi-synthetic penicillins of the present invention are useful as antibacterial agents for the treatment of bacterial infections caused by gram-positive and gram-negative bacteria including especially Pseudomonas strains.

2. Description of the Prior Art

It is well-known that penicillin antibiotics generally inhibit the growth of various gram-positive and gram-negative bacteria and are effective in the treatment of infections caused by these organisms. It is also known that few penicillins exert any appreciable antimicrobial activity against Pseudomonas. For the last two decades, however, the incidence of Pseudomonas aeruginosa infection has progressively increased. Recently, some penicillin antibiotics have been synthesized which are reported to be useful as antipseudomonal antibiotics (e.g. carbenicillin, U.S. Pat. No. 3,142,673; sulbenicillin, U.S. Pat. No. 3,660,379; and ticarcillin, U.S. Pat. No. 3,282,926), but these penicillins exhibit only a relatively low potency against Pseudomonas aeruginosa necessitating the use of large amounts of them for effective treatment. Therefore, there remains a need for the synthesis of new penicillins which possess a high degree of anti-Pseudomonas activity.

Various N-acyl derivatives of ampicillin (or a derivative thereof in which the phenyl ring is replaced by substituted phenyl, thienyl or another aryl or heterocyclic radical) have been disclosed in the patent and scientific literature. Illustrative of those patents and patent publications disclosing such derivatives containing an α-heterocyclic-carboxamido group are:

a. U.S. Pat. No. 3,945,995 disclosing penicillins of the formula where R is an unsubstituted phenyl group or a substituted phenyl group having one or more hydroxyl groups or a cyclohexadienyl group and A represents a monocyclic or polycyclic nitrogen-containing heterocyclic aromatic ring. Triazine is listed in the disclosure as being included within the definition of substituent "A," but no penicillins having a triazine "A" group are illustrated or exemplified (see also U.S. Pat. No. 4,005,075).

b. U.S. Pat. No. 3,953,428 disclosing ampicillin derivatives of the formula where R is selected from various nitrogen, sulfur or oxygen-containing mono-, bi- or polycyclic heterocyclic rings. Triazine "R" substituents are not included within the scope of the disclosure.

c. Japanese Patent Publication No. 72189/73 (Farmdoc 79353U) disclosing penicillins of the formula where $R^1$ and $R^2$ are hydrogen, $NH_2$, acylamino, alkylamino, OH, alkoxy, SH or alkylthio and X is N or CH. No penicillins are illustrated or exemplified having X=N, i.e. a 1,3,5-triazine ring.

d. U.S. Pat. No. 3,873,523 disclosing penicillins of the formula where $R^1$ is one of several named alicyclic, aryl or heterocyclic radicals, $R^2$ is hydrogen or, taken together with $R^1$ represents the group and $R^3$ is hydrogen or methyl (see also U.S. Pat. No. 3,948,903).

e. U.S. Pat. No. 3,951,955 disclosing penicillins of the formula where A is a substituted or unsubstituted condensed aromatic carbocyclic or heterocyclic ring, R is hydrogen or lower alkyl, X is oxygen or sulfur, Y is hydrogen, lower alkyl, lower alkanoyl or lower alkoxycarbonyl and Z is phenyl or thienyl. (See also U.S. Pat. No. 3,864,329).

f. U.S. Pat. No. 3,954,733 disclosing penicillins of the formula where A is a benzene ring or a 5 or 6-membered heteroaromatic ring containing 1 or 2 nitrogen atoms, Z is a nitrogen atom or a methylene group, X is an oxygen or sulfur atom, Y is hydrogen, lower alkoxycarbonyl or lower alkanoyl, $R_1$ is hydroxyl or protected hydroxyl and $R_2$ and $R_3$ are hydrogen or halogen.

g. U.S. Pat. No. 3,954,734 disclosing compounds of the formula where $R_3$ is phenyl, p-hydroxyphenyl, 2-thienyl or cyclohexadienyl, R is hydrogen or methyl, $R_1$ and $R_2$ are hydrogen, $C_1$-$C_6$ alkyl or $R_1R_2N$ taken together is nitro or certain cyclic amines, X is hydrogen, chlorine or bromine and Y is hydrogen or bromine.

h. U.K. Pat. No. 1,440,216 disclosing compounds of the formula where $R_1$ is hydrogen and $R_2$ is optionally substituted phenyl, thienyl or furyl, n or m independently are 0 or 1 and B represents one of several named pyrimidyl radicals.

i. U.S. Pat. No. 3,320,240 disclosing compounds of the formula where R is an optionally substituted alkyl, aralkyl, aryl or heterocyclic group and X is a direct linkage or a divalent aliphatic, aromatic or heterocyclic radical which may be substituted.

j. U.S. Pat. No. 3,993,642 disclosing compounds of the formula where $R_1$ is hydrogen, $C_1$-$C_5$ alkyl, monoaralkyl, monoaryl, substituted monoaryl or thienyl, A is one of several named bivalent radicals including inter alia defined above for $R_1$, E is oxygen or sulfur and B is optionally substituted phenyl or a thienyl, cyclohexenyl or cyclohexadienyl radical. (See also U.S. Pat. Nos. 3,923,789 and 3,974,288).

k. U.S. Pat. No. 3,939,150 disclosing penicillins of the formula where B is p-hydroxyphenyl or cyclohexadienyl, A is a 5- or 6- membered single or fused ring which may contain one or more nitrogen atom, an oxygen atom or a sulfur atom and $R^1$, $R^2$ and $R^3$ each represent hydrogen, hydroxy, lower alkyl, nitro, halogen or an oxo group. No triazine "A" rings are disclosed in this patent.

l. French Patent Publication No. 2,191,556 (Farmdoc 23502U) disclosing penicillins of the formula where R' is lower alkyl and R° is phenyl or chloro-substituted phenyl.

m. U.S. Pat. No. 3,433,784 disclosing penicillins of the formula where R is phenyl or thienyl, R' is optionally substituted heterocyclic and $n$ is 0 or 1. No compounds are disclosed where $n=0$ and R' is a triazine radical.

n. West German Published Application No. 2,312,976 (Farmdoc 59216U) disclosing penicillins of the formula where is a heteroaromatic ring with 6 ring atoms of which 1 or 2 are nitrogen atoms, Y is hydrogen, (lower)-alkanoyl or (lower)alkoxy-carbonyl and $R_1$ and $R_2$ are each inter alia hydroxyl.

o. Japanese Patent Publication No. 52790/73 (Farmdoc 64733U) disclosing the penicillin of the formula and p. West German Published Application No. 2,457,464 disclosing penicillins of the formula where A is optionally substituted phenyl, optionally substituted monocyclic aromatic heterocyclic or dihydrophenyl and X is —$SO_2$—, —CO—, —P(R)— or —P(O)(R) in which R is optionally substituted lower-molecular alkyl, alkenyl, alkoxy, aralkyl, aralkoxy, aryl or aryloxy.

SUMMARY OF THE INVENTION

The present invention comprises certain novel penicillin derivatives, methods for the preparation of said derivatives and pharmaceutical compositions comprising as the active ingredient(s), either (a) one of said penicillin derivatives or (b) one of said penicillin derivatives in combination with amikacin (1-[L-(—)-α-amino-α-hydroxybutryl]-kanamycin A) or a pharmaceutically acceptable acid addition salt thereof. More particularly, the present invention provides the novel penicillin derivatives having the formula

I wherein Z is an oxygen or sulfur atom and their pharmaceutically acceptable salts and physiologically hydrolyzed esters including especially the pivaloyloxymethyl, acetoxymethyl, methoxymethyl, phthalidyl and indanyl esters.

The pharmaceutically acceptable salts referred to above include nontoxic metallic salts such as sodium, potassium, calcium and magnesium, the ammonium salt and substituted ammonium salts, e.g. salts of such nontoxic amines as trialkylamines (e.g. triethylamine), procaine, dibenzylamine, N-benzyl-β-phenethylamine, 1-ephenamine, N,N'-dibenzyl-ethylenediamine, dehydroabietylamine, N,N'-bis(dehydroabietyl)ethylenediamine, N-(lower)alkyl-piperidine (e.g. N-ethylpiperidine) and other amines which have been used to form pharmaceutically acceptable salts of penicillins and cephalosporins. The most preferred salts are the alkali metal salts, i.e. the sodium and potassium salts.

As used herein the term "physiologically hydrolyzed esters" refers to those pharmaceutically acceptable esters (of penicillins or cephalosporins) known in the art to hydrolyze to the free acid form in vivo. Esters of this type are described, for example, in U.S. Pat. Nos. 3,859,274, 3,860,570, 3,860,579, 3,864,331, 3,873,521 and 3,919,196, in U.K. Patent Specifications 1,215,812, 1,267,936, 1,425,571, and 1,400,584, and in German Published Applications 1,951,012 and 2,230,620. Examples of suitable physiologically hydrolyzed esters include acetoxymethyl, pivaloyloxymethyl, α-acetoxyethyl, α-acetoxybenzyl, α-pivaloyloxyethyl, phthalidyl(3-phthalidyl), indanyl(5-indanyl), methoxymethyl, benzoyloxymethyl, α-ethylbutyryloxymethyl, propionyloxymethyl, valeryloxymethyl and isobutyryloxymethyl. The preferred esters are the acetoxymethyl, pivaloyloxymethyl, methoxymethyl, phthalidyl and 5-indanyl esters, most preferably acetoxymethyl, methoxymethyl and pivaloyloxymethyl.

Included within the scope of this invention are the optically active isomeric forms and mixtures thereof which arise by virtue of the asymmetric α-carbon atom of the 6-acyl side chain, i.e. the asterisked carbon atom shown in formula I above. These are the D- and L-epimers and the DL-form which is a mixture of the two optically active isomers. The D-form of the compounds of the present invention is the preferred form because of its greater activity relative to that of the L- or the DL-forms.

While the heterocyclic N-acyl groups of the penicillins of formula I are shown above in the keto form, the tautomeric enol forms, i.e. where the keto groups are shown as hydroxyl groups, are also included within the scope of the present invention.

DETAILED DESCRIPTION OF THE INVENTION

The novel and valuable penicillins of formula I may be prepared according to one procedure by reacting a compound of the formula (preferably the compound having the D-configuration in the 6-side chain, i.e. amoxicillin) or a salt or easily cleavable ester thereof with an acylating agent of the formula wherein Z is an oxygen or sulfur atom or a reactive acylating derivative thereof and, if the reaction product contains an easily cleavable ester protecting group, optionally removing said protecting group by a method known per se and, if desired, converting by a method known per se (a) the product in the form of a free acid to a pharmaceutically acceptable salt or a physiologically hydrolyzed ester thereof, or (b) the product in the form of a salt to the free acid or a pharmaceutically acceptable salt or a physiologically hydrolyzed ester thereof. The above acylation reaction may be carried out by methods which are themselves known in the art, e.g. from the synthesis of peptides, penicillins and cephalosporins.

The starting material penicillin of formula II is a known compound and is disclosed, for example, in U.S. Pat. Nos. 3,192,198 and 3,674,776. Preparation of the acylating acid starting material III has also been disclosed in the literature, e.g. in J. Am. Chem. Soc., 78, 1938 (1956) and J. Am. Chem. Soc., 78, 1258 (1956).

In the acylation of the α-amino group of penicillin II, the carboxylic acid of formula III may be used per se in which case it is preferred to use an enzyme or a condensing agent. Suitable condensing agents include N,N'-dimethylchloroforminiminium chloride, an N,N'-carbonyldiimidazole or an N,N'-carbonylditriazole, a carbodiimide reagent (especially N,N'-dicyclohexylcarbodiimide, N,N'-diisopropylcarbodiimide or N-cyclohexyl-N'-(2-morpholinoethyl)carbodiimide, alkylylamine, reagent, an isoxasolium salt reagent, keteni-mine reagent, hexachlorocyclotriphosphatriazine or hexabromocyclotriphosphatriazine, diphenylphosphoryl azide (DPPA), diethylphosphorylcyanide (DEPC), diphenylphosphite or N-ethoxycarbonyl-2-ethoxy-1,2-dihydroquinoline (EEDQ).

As an alternative to using the carboxylic acid III in the above process, there may also be employed reactive acylating derivatives of acid III, i.e. functional equivalents of the acid as acylating agents for a primary amino group. Examples of reactive acylating derivatives of the carboxylic acid include the acid halide (e.g. acid chloride or acid bromide), acid anhydrides, including mixed anhydrides (e.g. alkoxyformic anhydrides), acid azides, active esters (e.g. p-nitrophenyl) and active thioesters. Another reactive derivative of the acid is a corresponding azolide, i.e. an amide of the acid whose amide nitrogen is a member of a quasiaromatic five-membered ring containing at least two nitrogen atoms, i.e. imidazole, pyrazole, the triazoles, benzimidazole, benzotriazole and their substituted derivatives. The general method for preparation of azolides is described, for example, in U.S. Pat. No. 3,910,900.

Mention was made above of the use of enzymes to couple the free acid with compound II. Included in the scope of such processes are the use of an ester, e.g. the methyl ester, of that free acid with enzymes provided by various microorganisms, e.g. those described in J. Am. Chem. Soc., 94(11), 4035–4037 (1972), J. Antibiotics (Japan), 24(5), 321–323 (1971) and U.S. Pat. No. 3,682,777.

Acylation with the carboxylic acid III or reactive acylating derivative thereof may be carried out on the penicillanic acid of formula II or a salt (e.g. an alkali metal or an amine salt) or easily cleavable ester thereof.

The term "easily cleavable ester" refers to a derivative of the penicillanic acid in which the 3-carboxyl group has been protected by any of the known ester protective groups capable of being removed following the acylation reaction by methods, e.g. chemical or enzymatic hydrolysis, treatment with chemical reducing agents under mild conditions, irradiation with ultraviolet light or catalytic hydrogenation, which do not result in any appreciable destruction of the remaining portion of the molecule. Examples of suitable "easily cleavable esters" include trialkylsilyl (e.g. trimethylsilyl) and other esters derived from silyl alcohol or stannyl alcohol which can be removed by solvolysis with a solvent containing hydroxyl groups, t-butoxycarbonyl, benzhydryl, benzyl, p-nitrobenzyl, p-methoxybenzyl, 2,2,2-trichloroethyl, phenacyl, acetonyl, p-bromophenacyl, (lower)alkyl such as methyl, ethyl or t-butyl and the physiologically hydrolyzed esters mentioned above. The general methods for the preparation of these esters and for their removal are described in the literature and are well-known to those skilled in the art.

The acylation process is conducted in a reaction-inert solvent system which can be aqueous or non-aqueous. Suitable reaction-inert solvents include, for example, water, acetone, tetrahydrofuran, dioxane, acetonitrile, dimethylformamide, dimethylsulfoxide, methylene chloride, chloroform, benzene, toluene, methyl isobutyl ketone and mixtures of the above-mentioned organic solvents with water. The choice of solvent, i.e. particularly whether an aqueous or non-aqueous solvent is used, is dependent on the particular starting materials employed. Thus, for example, if the penicillin starting material II is used in the form where the 3-carboxyl moiety is protected by an ester group cleaved by hydroxylic solvents, e.g. a silyl or stannyl ester, an aprotic organic solvent is most preferably employed. Also, when the penicillin of formula II is used in its salt form, water or an aqueous organic solvent system is preferably employed. The most advantageous solvent system for the particular reagents used can be determined by routine experimentation.

The duration and temperature of the acylation reaction are not critical. Temperatures in the range of from about −30° C. to about +50° C. are commonly used for reaction times ranging from less than one hour up to a day or more. Although the initial contacting of the reactants is preferably carried out at around 0° C. to reduce the incidence of by-products, it is frequently desirable after a few minutes of mixing to allow the reaction mixture to warm to room temperature until the reaction is complete.

The reactants of formulae II and III are normally employed in approximate equimolar quantities, although an excess of either can be used if desired.

When a carboxyl-protecting group is present in the product of the acylation reaction, it may be eliminated, if desired, in a per se conventional manner to give the desired 3-carboxylic acid penicillin or a salt thereof.

The acylation product is isolated in a conventional manner as the free acid or as a salt or as a physiologically hydrolyzed ester (if the appropriate ester group has been used in the acylation process). The free acid can be converted to a pharmaceutically acceptable salt thereof by treatment with an appropriate organic or inorganic base. The carboxylate salts may be converted to the free acids by treatment with an acid or suitable ion exchange resin. The product in the form of the free acid or salt thereof may also be converted by known methods to a corresponding physiologically hydrolyzed ester such as the pivaloyloxymethyl, acetoxymethyl, phthalidyl, 5-indanyl or methoxymethyl esters.

An alternative process for preparing the penicillins of formula I comprises reacting 6-aminopenicillanic acid or a salt or easily cleavable ester thereof with an acylating agent of the formula

IV wherein Z is an oxygen or sulfur atom (preferably having the D-configuration at the α-carbon atom) or a reactive acylating derivative thereof and, if the reaction product contains an easily cleavable ester protecting group, optionally removing said protective group by a method known per se and, if desired, converting by methods known per se (a) the product in the form of a free acid to a pharmaceutically acceptable salt or a physiologically hydrolyzed ester thereof, or (b) the product in the form of a salt to the free acid or a pharmaceutically acceptable salt or a physiologically hydrolyzed ester thereof.

The terms "easily cleavable ester," "reactive acylating derivative", "pharmaceutically acceptable salt" and "physiologically hydrolyzed ester" used above in the description of the alternative process are as defined previously.

The acylation conditions, i.e. solvents, temperatures, molar ratios and isolation procedures, for this process are substantially the same as those described in connection with the first-mentioned process.

Carboxylic acid starting material IV may be prepared by the reaction of p-hydroxyphenylglycine, preferably D(−)-2-(p-hydroxyphenyl)glycine, with the carboxylic acid of formula III or a reactive acylating derivative thereof in substantially the same manner as that for the other acylation steps described above.

The penicillins provided by the present invention are useful as antimicrobial agents against various gram-positive and gram-negative bacteria including especially Pseudomonas and may be used in the same manner as other commercially available penicillins such as ampicillin or amoxicillin. In the treatment of bacterial infections in man, the compounds of this invention are preferably administered parenterally in an amount of from about 15 to 150 mg./kg./day in divided dosage, e.g. 3 to 4 times a day. They are administered in dosage units containing, for example, 125, 250 or 500 mg. of active ingredient, with suitable physiologically acceptable carriers or diluents. The dosage units are preferably in the form of liquid preparations such as solutions or suspensions.

The compounds of the present invention have been found to be particularly effective against Pseudomonas organisms. As of today, the standard commercially available penicillin used against Pseudomonas infections is carbenicillin. As demonstrated below, the penicillins of the present invention show vastly superior activity (relative to carbenicillin) both in vitro and in vivo against Pseudomonas strains.

A sample of sodium D(−)-6-(α-(1,2,4-triazine-3,5-dione-6-carboxamido)-4-hydroxyphenylacetamido)-penicillanate (BL-P1908) after solution in water and dilution with Mueller-Hinton medium was found to exhibit the following Minimum Inhibitory Concentrations (M.I.C.) in mcg./ml. versus the indicated Pseudomonas strains as determined by overnight incubation at 37° C. by agar dilution. A carbenicillin sample was also run for comparative purposes.

|  | M.I.C. in mcg./ml. Compound | |
|---|---|---|
| Pseudomonas aeruginosa strain | BL-P1908 | Carbenicillin |
| A9502 | 2 | 63 |
| A9827 | 1 | 32 |
| A9843A | 0.5 | 32 |
| A9910 | 1 | 32 |
| A9923 | 2 | 63 |
| A9924 | 2 | 63 |
| A9925 | 1 | 32 |
| A9926 | 1 | 63 |
| A9930 | 2 | 63 |
| A9931 | 1 | 63 |
| A15150 | 2 | 32 |
| A15151 | 8 | 32 |
| A15194 | 4 | >125 |
| A15195 | 2 | 63 |
| A15196 | 2 | 63 |
| A20125 | 2 | 63 |
| A20126 | 0.5 | 16 |
| A20127 | 1 | 63 |
| A20128 | 1 | 63 |
| A20129 | 1 | 63 |
| A20130 | 1 | 63 |
| A20227 | 0.5 | 32 |
| A20228 | 1 | 63 |
| A20546 | 2 | 63 |
| A20557 | 4 | >125 |
| A20574 | 0.5 | 32 |
| A20602 | 2 | 63 |
| A20616 | 1 | 63 |
| A20641 | 0.5 | 63 |
| A20717 | 4 | >125 |
| A20726 | 1 | 63 |
| A21336 | 2 | 63 |

A sample of sodium D(—)-6-(α-(1,2,4-triazine-3-thione-5-one-6-carboxamido)-4-hydroxyphenylacetamido)-penicillanate (BL-P1937) after solution in water and dilution with Mueller-Hinton broth was found to exhibit the following Minimum Inhibitory Concentrations (M.I.C.) in mcg./ml. versus the indicated Pseudomonas strains as determined by overnight incubation at 37° C. by tube dilution. Results of three tests were as follows:

|  | M.I.C. in mcg./ml. | | |
|---|---|---|---|
| Pseudomonas aeruginosa strain | Test 1 BL-P1937 | Test 2 BL-P1937 | Test 3 BL-P1937 |
| A9843A | 1 | 2 | 2 |
| A20574 | 4 | 2 | 2 |
| A20557 | 2 | 4 | 4 |
| A20717 | 16 | 32 | 16 |
| A20726 | 2 | 8 | 8 |
| A20641 | 8 | 8 | 8 |
| A20546 | 2 | 2 | 2 |
| A21336 | 4 | 8 | 4 |
| A20126 | 16 | 8 | 4 |
| A20128 | 2 | 2 | 2 |
| A20227 | 4 | 4 | 2 |
| A9910 | 1 | 2 | 4 |
| A9926 | 2 | 4 | 2 |
| A20616 | 2 | 4 | 4 |
| A20602 | 4 | 8 | 2 |
| A20228 | 2 | 8 | 2 |

The bactericidal in vitro activity of sodium D(—)-6-(α-(1,2,4-triazine-3,5-dione-6-carboxamido)-4-hydroxyphenylacetamido)penicillanate (BL-P1908) against several strains of *Pseudomonas aeruginosa* was determined under two sets of conditions. In one test the Minimum Bactericidal Concentrations (M.B.C.) were determined using an inoculum size of $10^4$ cells/ml. and the M.B.C. was defined as the lowest concentration of antibiotic in mcg./ml. needed to kill at least 99% of the viable Pseudomonas cells. Comparative M.B.C. results for carbenicillin and BL-P1908 under these test conditions are shown in the table below.

|  | M.B.C. in mcg./ml. Compound | |
|---|---|---|
| Pseudomonas aeruginosa strain | BL-P1908 | Carbenicillin |
| 9843A | 63 | 63 |
| 20574 | 2 | 63 |
| 20557 | 16 | 250 |
| 20717 | 63 | 250 |
| 20726 | 2 | 125 |
| 20641 | 4 | 125 |
| 20546 | 1 | 63 |
| 21336 | 2 | 63 |
| 20126 | 2 | 63 |
| 20128 | 2 | 63 |
| 20227 | 2 | 63 |
| 9910 | 1 | 32 |
| 9926 | 2 | 63 |
| 20616 | 2 | 125 |
| 20228 | 8 | 63 |

The effect of increased inoculum size on the bactericidal activity of BL-P1908 was investigated by a second test in which an inoculum size of $10^5$ cells/ml. was used and the M.B.C. was defined as the lowest concentration of antibiotics in mcg./ml. needed to kill at least 99.9% of viable Pseudomonas cells. Comparative M.B.C. results for carbenicillin and BL-P1908 under these conditions are shown below.

|  | M.B.C. in mcg./ml. Compound | |
|---|---|---|
| Pseudomonas aeruginosa strain | BL-P1908 | Carbenicillin |
| 9843A | 500 | 125 |
| 20574 | >1000 | 125 |
| 20557 | 1000 | 250 |
| 20717 | >1000 | 1000 |
| 20726 | 1000 | 250 |
| 20641 | 1000 | 125 |
| 20546 | 500 | 250 |
| 21336 | 1000 | 125 |
| 20126 | 32 | 63 |
| 20128 | 16 | 125 |
| 20227 | 4 | 125 |
| 9910 | 500 | 125 |
| 9926 | 250 | 125 |
| 20616 | 1000 | 250 |
| 20602 | 1000 | 250 |
| 20228 | 250 | 63 |

The bactericidal in vitro activity of BL-P1937 against *Pseudomonas aeruginosa* strains was also determined. Three tests were run, using initial inoculum sizes of 2.4 × $10^5$, 1.6 × $10^5$ and 1.4 × $10^5$ cells/ml., respectively, and the M.B.C. was defined as the lowest concentration of antibiotic in mcg./ml. needed to kill at least 99.9% of viable Pseudomonas cells. The results of the tests are shown below.

|  | M.B.C. in mcg./ml. | | |
|---|---|---|---|
| Pseudomonas aeruginosa strain | Test 1* BL-P1937 | Test 2** BL-P1937 | Test 3*** BL-P1937 |
| A9843A | 125 | 250 | 250 |
| A20574 | 250 | 250 | 500 |
| A20557 | 250 | 1000 | 500 |
| A20717 | 500 | 1000 | >1000 |
| A20726 | 32 | 250 | 500 |
| A20641 | 125 | 250 | 250 |
| A20546 | 250 | 1000 | 500 |
| A21336 | 250 | 500 | 500 |
| A20126 | 16 | 63 | 63 |
| A20128 | 16 | 16 | 63 |
| A20227 | 63 | 8 | 16 |
| A9910 | 125 | 250 | 500 |
| A9926 | 250 | 1000 | 250 |
| A20616 | 125 | 250 | 500 |

| Pseudomonas aeruginosa strain | M.B.C. in mcg./ml. | | |
|---|---|---|---|
| | Test 1* BL-P1937 | Test 2** BL-P1937 | Test 3*** BL-P1937 |
| A20602 | 250 | 500 | 500 |
| A20228 | 125 | 500 | 250 |

*initial inoculum size $2.4 \times 10^5$
**initial inoculum size $1.6 \times 10^5$
***initial inoculum size $1.4 \times 10^5$ Plasma antibiotic levels from mice administered a single intramuscular dose of 40 mg./kg. of BL-P1908 or carbenicillin are shown in the following table.

| Mouse Blood Levels: BL-P1908 | | | | | |
|---|---|---|---|---|---|
| | | Blood Level (μg./ml.) Min. after Admin. | | | |
| Compound | | 15 | 30 | 60 | 90 |
| BL-P1908 | | | | | |
| | Test 1 (Ave. of 6 mice tested) | 24.9 | 19.4 | 7.5 | <3.9 |
| | Test 2 (Ave. of 8 mice tested) | 28.4 | 15.1 | 3.0 | <1.8 |
| | Ave. | 26.7 | 17.3 | 5.3 | <2.9 |
| Carbenicillin | Literature values | 18.1 | 8.1 | <4.6 | <4.6 |
| | Test 1 (Ave. of 6 mice tested) | 19.1 | 12.5 | 4 | <1.4 |
| Assay organism: | P. aeruginosa A20235-2 for carbenicillin B. subtilis A9506 for BL-P1908 | | | | |

Serum antibiotic levels from mice administered a single intramuscular dose of 40 mg./kg. of BL-P1937 or carbenicillin are shown below.

| Mouse Blood Levels: BL-P1937 | | | | |
|---|---|---|---|---|
| | Blood Level (μg./ml.) Min. after Admin. | | | |
| Compound | 15 | 30 | 60 | 90 |
| BL-P1937 | 19.9 | 10.3 | <2.2 | <2.2 |
| *Carbenicillin | 18.1 | 8.1 | <4.6 | <4.6 |
| Assay organisms: | P. aeruginosa A20235-2 for carbenicillin B. subtilis A9506 for BL-P1937 | | | |

*Literature values

The in vivo activities of BL-P1908 and BL-P1937 against Pseudomonas aeruginosa are shown below comparatively with carbenicillin. Treatment with the drugs (administered by the intramuscular route) was initiated immediately after inoculation with the infecting organism and again at two hours after inoculation. The $PD_{50}$ (dose in mg./kg. required to give protection to 50% of the infected mice) per treatment of BL-P1908, BL-P1937 and carbenicillin versus Pseudomonas aeruginosa A9843A and A20599 are given below.

| Protective Effect in the Intramuscular Treatment of Systemically Infected Mice | | | | |
|---|---|---|---|---|
| | Challenge | $PD_{50}$/treatment (mg./kg.) | | |
| Organism | (No. of Organisms) | BL-P1937 | BL-P1908 | Carbenicillin |
| P. aeruginosa A9843A | $1 \times 10^4$ | 11 | 4.8 | 100* |
| | $2 \times 10^4$ | 5.4 | 2.5 | 100* |
| | $3 \times 10^4$ | 11 | 11 | 130 |
| P. aeruginosa A20599 | $3 \times 10^4$ | ca. 13 | 5.4 | 100 |
| | $6 \times 10^4$ | 22 | 9.6 | 130 |

*Typical figures based on several tests.

The compounds of the present invention have also been found to possess activity against anaerobic bacteria as illustrated by the M.I.C. data below for several strains of Bacteroides fragilis and various Clostridium species.

| Organism | M.I.C. in mcg./ml. | | |
|---|---|---|---|
| | BL-P1937 | BL-P1908 | Carbenicillin |
| Bacteroides fragilis A20926 | 2 | 2 | 16 |
| Bacteroides fragilis A20927-1 | 1 | 1 | 2 |
| Bacteroides fragilis A20920 | 0.5 | 1 | 2 |
| Bacteroides fragilis A20930 | 16 | 16 | 63 |
| Bacteroides fragilis A22053 | 2 | 8 | 63 |
| Bacteroides fragilis A27020 | 8 | 16 | >125 |
| Bacteroides fragilis A20933 | 4 | 8 | 32 |
| Bacteroides fragilis A20934 | 4 | 4 | 32 |
| Bacteroides fragilis A20935 | 2 | 1 | 32 |
| Bacteroides fragilis A21870 | 1 | 16 | 4 |
| Bacteroides fragilis A21871 | 2 | 16 | 32 |
| Bacteroides fragilis A21872 | 16 | 16 | 63 |
| Bacteroides fragilis A21875 | 8 | 4 | 16 |
| Clostridium species | | | |
| Cl. acidiurici A9560 | 1 | 1 | 0.5 |
| Cl. chauvoei A9561 | 1 | 4 | 0.5 |
| Cl. cylindrosporum A9562 | 0.25 | 16 | 0.5 |
| Cl. difficile A21675 | 4 | 2 | 32 |
| Cl. septicum A21869 | 1 | 1 | 1 |
| Cl. perfringens A21873 | 0.063 | 0.13 | 0.5 |
| Cl. perfringens A21874 | 0.13 | 0.13 | 0.5 |
| Cl. ramosum A21883 | 0.25 | 0.25 | 32 |
| Cl perfringens A21907 | 0.25 | 0.13 | 4 |
| Cl. ramosum A21970 | 2 | 2 | 32 |
| Cl. difficile A21972 | 4 | 4 | 32 |

While, as indicated above, the penicillin derivatives of the present invention are useful antibacterial agents in themselves, it has been found that they are particularly useful when used in combination with the aminoglycoside antibiotic, amikacin (or a pharmaceutically acceptable acid addition salt thereof), disclosed, for example, in U.S. Pat. No. 3,781,268. In another aspect, therefore, the present invention provides a pharmaceutical composition comprising (a) a penicillin derivative of the formula wherein Z is an oxygen or sulfur atom or a pharmaceutically acceptable salt or physiologically hydrolyzed ester thereof as defined above and (b) the aminoglycoside antibiotic, amikacin (1-[L-(—)-γ-amino-α-hydroxybutryl]kanamycin A), or a pharmaceutically acceptable acid addition salt thereof, optionally in admixture with a pharmaceutically acceptable carrier or diluent. The penicillin-aminoglycoside compositions have been found to provide both a synergistic inhibitory effect and a synergistic bactericidal effect against various strains of Pseudomonas aeruginosa.

As used herein, the term "pharmaceutically acceptable acid addition salt" used in reference to amikacin refers to those pharmaceutically acceptable acid addition salts disclosed in U.S. Pat. No. 3,781,268 as being included within the scope of the invention claimed therein. Thus, suitable salts of amikacin include mono-, di-, tri- or tetra salts formed with such pharmaceutically acceptable acids as acetic, hydrochloric, sulfuric, maleic, phosphoric, nitric, hydrobromic, ascorbic, malic and citric acids. A most preferred amikacin salt is amikacin disulfate (amikacin sulfate).

Pharmaceutical compositions comprising both the penicillin of formula I (or a pharmaceutically acceptable salt or a physiologically hydrolyzed ester thereof) and amikacin (or a pharmaceutically acceptable acid addition salt thereof) possess many advantages over compositions comprising only one or the other of the two antibiotic components. Thus, a broadened antibacterial spectrum can be achieved since amikacin is antibacterially effective against organisms not affected by the penicillin, and vice versa. The potential nephrotoxicity and ototoxicity problems associated with the aminoglycoside antibiotic can be reduced by administration of a synergistic antibacterial combination product which permits a lower dosage of the aminoglycoside to achieve the same therapeutic effect. Reduced amikacin doses made possible by the synergistic combination product might also allow patients suffering from Pseudomonas infections to be treated with this highly effective antibiotic composition for a longer period of time than currently recommended for amikacin therapy (currently a 15 day limit is recommended). Finally, the synergistic antibacterial effects seen in vitro and in animal studies if carried over into clinical experience might be expected to favorably influence the clinical outcome of patients receiving the antibiotic combination (see, for example, review by J. Klastersky in *Clinics in Hematology*, Vol. 5, 1976, pg. 361–376).

The synergistic antibacterial activity of the combinations provided by the present invention is shown and verified by the following tests.

Figure 1:
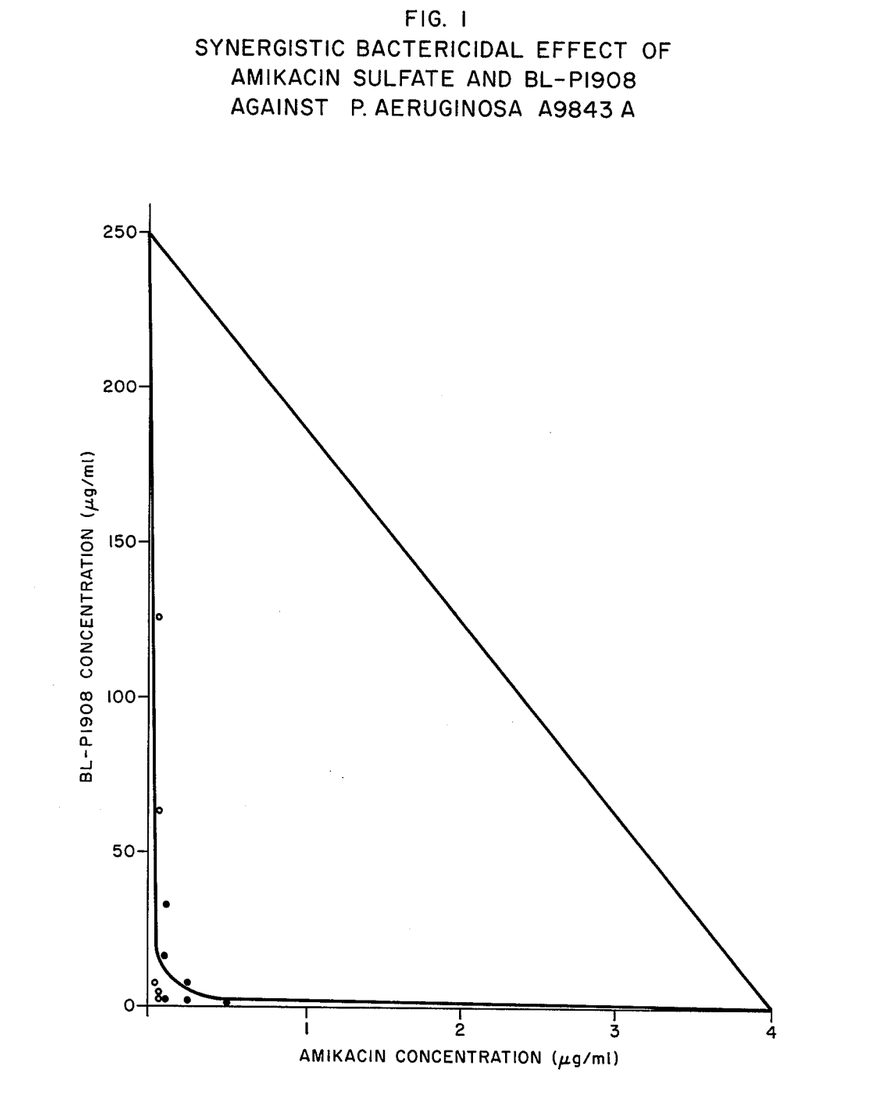
FIG. 1 shows the synergistic bactericidal effect of amikacin sulfate and BL-P1908 against P. aeruginosa A9843A

The in vitro synergism of a combination of BL-P1908 and amikacin sulfate was tested by the broth dilution method described by Sabath, et al. in *Antimicrobial Agents and Chemotherapy*, 1966, pg. 149–155. Broth dilution sensitivity tests were performed according to the "checkerboard" pattern. The inoculum added was approximately $10^5$ cells/ml. and the medium used was Mueller-Hinton broth. Results (M.B.C.'s) were plotted on an arithmetic scale according to the method of Loewe (*Arzneimittel-Forsch*, Vol. 3, 1953, pg. 285–290) as reviewed by Lacey (*Symp. Soc. Gen. Microbiol.*, Vol. 8, 1958, pg. 247–288) for each strain of *Pseudomonas aeruginosa* tested as illustrated in FIG. 1 for the case in which the test organism was *Pseudomonas aeruginosa* strain A9843A.

In the above curve, open circles indicate that for a set of combinations consisting of a fixed concentration of one drug and variable concentrations of the second drug, the combination containing the lowest concentration of the latter was bactericidal, i.e., no endpoint was obtained. The actual MBC of the second drug in combination was therefore either equal to or less than the one plotted.

Concentrations of the penicillin and aminoglycoside have been plotted on the ordinate and abscissa, respectively. Each point represents the same biological effect, i.e. the lowest concentrations of antibiotic(s) required to kill 99.9% of the viable Pseudomonas organisms. The line joining the points for each pair of antibiotics is called an "isobol". If the isobol of a pair of drugs follows a straight line connecting the minimal bactericidal concentration of each drug independently, the effect is additive; if concave (bowing toward the coordinates), it represents synergism. Synergism, according to this test, is considered to exist whenever one antibiotic, at a concentration of 1/4th its M.B.C., reduces the M.B.C. of the other antibiotic at least 4-fold when they are in combination. In the curve illustrated, the combination of amikacin and BL-P1908 shows bactericidal synergism against *Pseudomonas aeruginosa* A9843A. Thus, as shown by the isobologram, a composition comprising about 0.125 mcg./ml. of amikacin sulfate and about 1 mcg./ml. of BL-P1908 provides the same bactericidal effect against strain A9843A as 250 mcg./ml. of BL-P1908 alone or 4 mcg./ml. of amikacin sulfate alone.

The above procedure was employed to investigate the in vitro bactericidal synergism of the BL-P1908/amikacin combination against five other strains of *Pseudomonas aeruginosa* of differing strain-types. When the results of strain A9843A are included, bactericidal synergism was seen with four of the six strains tested. The combination was synergistic against two strains, i.e. A9843A and A20552, which are sensitive to both BL-P1908 and amikacin, and two strains, i.e. A21509 and A21510, which are sensitive to BL-P1908 and resistant to amikacin. No synergism was seen for strain A20480 which is BL-P1908 resistant and amikacin sensitive. The combination displayed synergism against strain A20620 which is resistant to both BL-P1908 and amikacin, but the synergistic concentrations were not at clinically achievable levels of the antibiotics. The synergistic bactericidal effects of the four strains mentioned above are shown below.

| Pseudonomas aeruginosa strain | BL-P1908 | Minimum Bactericidal Concentration (mcg./ml.) | |
|---|---|---|---|
| | | Amikacin | BL-P1908/ Amikacin |
| A20552 | 500 | 8 | 0.5 μg./ml. amikacin and 1 μg./ml. BL-P1908 |
| A21510 | 100 | 64 | 4 μg./ml. amikacin and 4 μg./ml. BL-P1908 |
| A21509 | 500 | 125 | 4 μg./ml. amikacin and 4 μg./ml. BL-P1908 |
| A9843A | 250 | 4 | 0.125 μg./ml. amikacin and 1 μg./ml. BL-P1908 |

Figure 2:
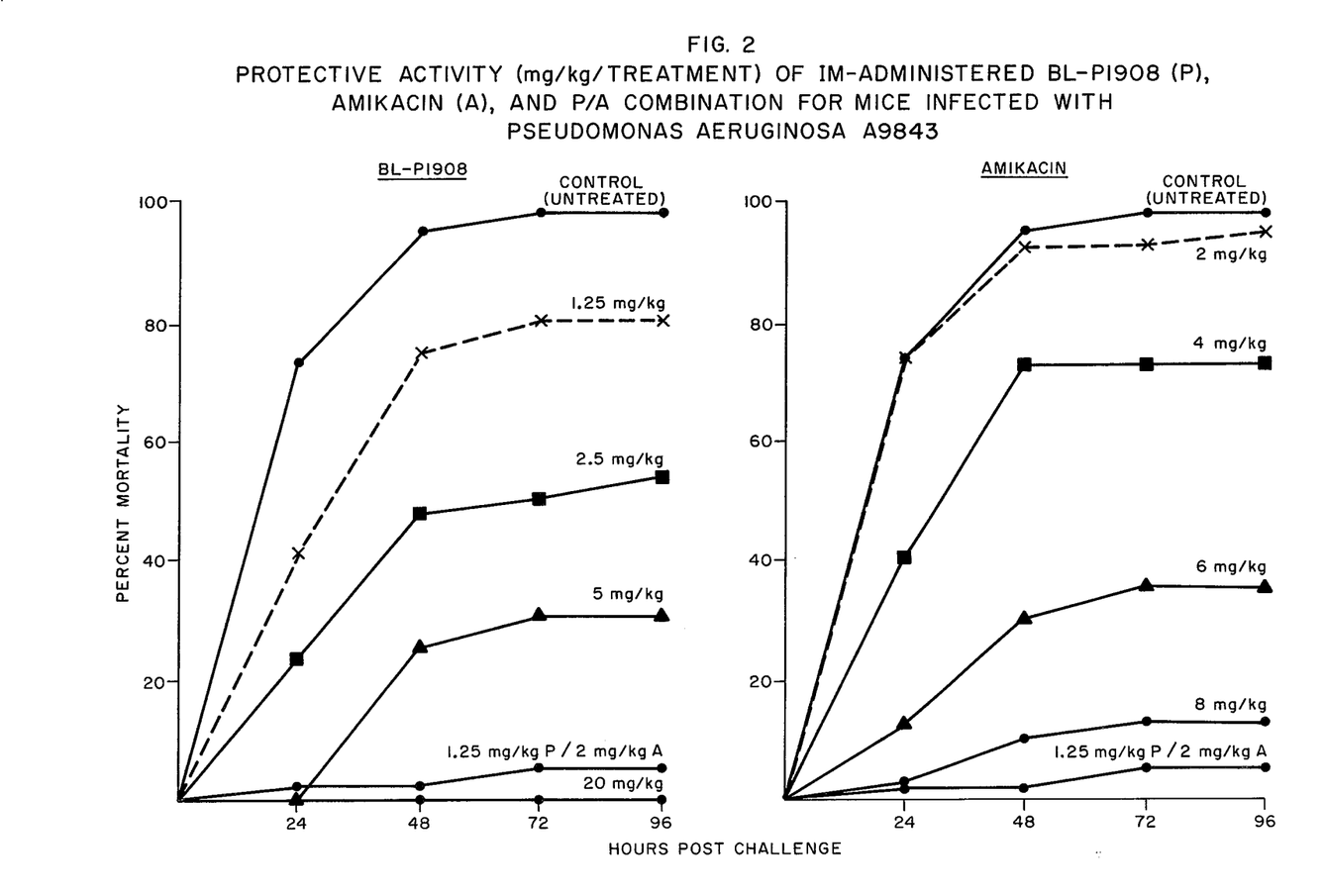
FIG. 2 shows the protective activity of intramuscularly-administered BL-P1908, amikacin and a BL-P1908/amikacin combination for mice infected with P. aeruginosa A9843A.

The in vivo synergism of the BL-P1908/amikacin combination was demonstrated for *Pseudomonas aeruginosa* A9843A. The killing curves for BL-P1908 and amikacin sulfate, alone and in combination, are shown in FIG. 2 (general procedure used which is described in Antibiot. Chemother., Vol. 2, 1952, pg. 243–247).

The data indicates that a combination of 1.25 mg./kg. of BL-P1908 and 2 mg./kg. of amikacin is as effective as dosages of 5 mg./kg. of BL-P1908 alone or 8 mg./kg. of amikacin alone.

The therapeutic penicillin-aminoglycoside compositions of the present invention may be administered to poultry and animals, including man, by injection. The compositions may have optionally incorporated therewith standard pharmaceutically acceptable solid or liquid carriers or diluents. Other suitable dosage unit forms may be prepared according to known methods of the pharmaceutical industry.

The relative amount of the active ingredients in the combination according to the present invention may vary between wide ranges depending on the particular organism being treated and the choice of the physician as to whether to favor one or the other of the antibiotic components in treating a particular patient. A preferred weight ratio of the components found to provide synergistic bactericidal results against the four *Pseudomonas aeruginosa* strains mentioned above is between about 1:2 (amikacin:penicillin) and 1:100. Compositions outside of this preferred range also provide advantageous results, however, and are intended to be included within the scope of the present invention. As an example of a proposed human dose, a parenteral preparation may be used comprising 200 mg. amikacin sulfate and 400 mg. of BL-P1908. The dry-fill containing the amikacin and penicillin is dissolved in sterile water and then administered by injection as a single dose of the antibiotic combination. This proposed single dose might be administered about twice a day as a proposed daily human dosage. The particular dosage selected will, of course, be determined by the physician after considering the age, weight and condition of the subject and is determinable by those skilled in the art based on data presented herein and experience with other known penicillin-aminoglycoside combinations.

Also provided by the present invention is a method for the treatment of antibacterial infections, particularly Pseudomonas infections, in poultry and animals, including man, which method comprises administration of an antibacterially effective dose of a penicillin-aminoglycoside composition as disclosed above.

Further details of the present invention are to be found in the following illustrative examples which are not intended to limit the scope of the invention.

Preparation of Starting Materials 1. 1,2,4-Triazine-3,5-dione-6-carboxylic acid The title compound can be prepared from ethyl oxomalonate by the procedure described by E. A. Falco, et al. in J. Amer. Chem. Soc., 78, 1938 (1956) and by R. B. Barlow, et al. in J. Amer. Chem. Soc., 78, 1258 (1956).

2. Ethyl 1,2,4-triazine-3,5-dione-6-carboxylate Anhydrous hydrogen chloride gas was bubbled into a suspension of 5.5 g. (0.035 mole) of 1,2,4-triazine-3,5-dione-6-carboxylic acid in 150 ml. of absolute ethyl alcohol for 5 minutes causing a solution. The solution was stirred at room temperature for 60 hours. The reaction mixture was concentrated in vacuo and cooled causing the product to crystallize. The product was filtered, washed with absolute ethyl alcohol and air dried. Recrystallization from 20 ml. of absolute ethyl alcohol gave 4.25 g. (65.7%) of ethyl 1,2,4-triazine-3,5-dione-6-carboxylate; m.p. 183°–186° C. The infrared and nuclear magnetic resonance spectra were consistent for the desired product.

Anal. Calc'd. for $C_6H_7N_3O_4$: C, 38.92; H, 3.81; N, 22.70; Found: C, 39.36; H, 3.94; N, 22.12. Found, corrected for 0.16% $H_2O$: C, 39.44; H, 3.93; N, 22.16.

3. 1,2,4-Triazine-3,5-dione-6-carboxylic acid hydrazide To a solution of 4.2 g. (0.023 mole) of ethyl 1,2,4-triazine-3,5-dione-6-carboxylate in 50 ml. of 95% ethyl alcohol, hydrazine (6 ml.) (64% in water) was added and a precipitate began to separate from the mixture. The reaction mixture was heated at reflux for 17 hours and then cooled. The product was filtered, washed with 95% ethyl alcohol and air dried giving 4.35 g. (91.3%) of 1,2,4-triazine-3,5-dione-6-carboxylic acid hydrazide as the hydrazine salt; decomp. 230°–260° C. The infrared spectrum was consistent for the desired product.

Anal. Calc'd. for $C_4H_9N_7O_3$: C, 23.65; H, 4.47; N, 48.26; Found: C, 24.06; H, 4.51; N, 48.43.

4. 1,2,4-Triazine-3,5-dione-6-carbonyl chloride A suspension of 1.56 g. (0.010 mole) of 1,2,4-triazine-3,5-dione-6-carboxylic acid in 100 ml. of methylene chloride, in an apparatus protected from atmospheric moisture, was gassed with dry hydrogen chloride for 5 minutes. Then 4.16 g. (0.020 mole) of phosphorus pentachloride was added to the suspension and the mixture was stirred at room temperature for 4 hours. Two additional spoonulas of phosphorus pentachloride, about 0.5 g. each, were added to the suspension and the mixture was stirred at room temperature for an additional 19 hours. Total reaction time was 23 hours. The suspended material was filtered off, washed well with methylene chloride and air dried giving 1.4 g. (79.0%) of 1,2,4-triazine-3,5-dione-6-carbonyl chloride[1], m.p. 189°–190° C. (gas evolution).

[1]. J. Daunis and M. Follet, Bull Soc. Chim. Fr., (11), 3178 (1973).

5. 1,2,4-Triazine-3-thione-5-one-6-carboxylic acid The title compound can be prepared from ethyl oxomalonate by the procedure described by E. A. Falco, et al. in J. Amer. Chem. Soc., 78, 1938 (1956) and by R. B. Barlow, et al. in J. Amer. Chem. Soc., 78, 1258 (1956).

6. 1,2,4-Triazine-3-thione-5-one-6-carbonyl chloride The title compound can be prepared by the procedure disclosed by J. Daunis and M. Follet, Bull. Soc. Chim. Fr., (11), 3178 (1973).

EXAMPLES

Example 1

Sodium D(−)-6-(α-(1,2,4-triazine-3,5-dione-6-carboxamido)-4-hydroxyphenylacetamido)penicillanate (acid azide method).

A. Preparation of acid azide acylating agent

A solution of 1.01 g. (0.005 mole) of 1,2,4-triazine-3,5-dione-6-carboxylic acid hydrazide hydrazine salt in 50 ml. of water, 20 ml. of 1N hydrochloric acid and 70 ml. of N,N-dimethylformamide was cooled to −3° C. A solution of 0.83 g. (0.012 mole) of sodium nitrite in 4 ml. of water was added to the hydrazide solution and the mixture was stirred at −3° C. to −5° C. for 30 minutes to give in solution the acid azide of 1,2,4-triazine-3,5-dione-6-carboxylic acid.

B. Coupling

A solution of 2.09 g. (0.005 mole) of D(−)-6-(α-amino)-4-hydroxyphenylacetamido penicillanic acid in 25 ml. of water and 10 ml. of tetrahydrofuran was obtained by the addition of 3.36 g. (0.04 mole) of sodium bicarbonate. The solution was cooled to 4° C. The acid azide solution was then added all at once to the penicillanic acid solution, followed by removal of the cooling bath and stirring of the reaction mixture at room temperature for 19 hours. The reaction mixture was filtered and the filtrate concentrated to near dryness at reduced pressure. The residue was dissolved in 50 ml. of water and the aqueous phase adjusted to pH 2.5 with 42% phosphoric acid. The aqueous phase was extracted 3 times with ethyl acetate. The combined organic extracts were washed 3 times with water and dried over sodium sulfate. After bubbling dry nitrogen through the ethyl acetate solution for 30 minutes, 1.8 ml. (0.005 mole) of sodium 2-ethylhexanoate was added to the solution causing the product to separate. After concentrating the solvent somewhat at reduced pressure, the product was filtered, washed with ethyl acetate and air dried. The solid was dissolved in 20 ml. of methanol, filtered and the filtrate diluted with 30 ml. of ethyl acetate causing the product to precipitate. The product was filtered, washed with acetone and air dried giving 0.188 g. (6.8%) of sodium D(−)-6-(α-(1,2,4-triazine-3,5-dione-6-carboxamido)-4-hydroxyphenylacetamido)penicillanate; decomp. 250°–260° C. The infrared and nuclear magnetic resonance spectra were consistent for the desired product.

Anal. Calc'd. for $C_{20}H_{18}N_6O_8SNa_2.4H_2O$: C, 38.71; H, 4.22; N, 13.55; $H_2O$, 11.6; Found: C, 3.05; H, 4.00; N, 13.17; $H_2O$, 10.67.

Example 2

Sodium D(−)-6-(α-(1,2,4-triazine-3,5-dione-6-carboxamido)-4-hydroxyphenylacetamido)penicillanate (mixed anhydride method).

A. Preparation of mixed anhydride acylating agent

A mixture of 0.78 g. (0.005 mole) of 1,2,4-triazine-3,5-dione-6-carboxylic acid, 0.7 ml. (0.005 mole) of triethylamine and 1.5 g. of Linde 4A molecular sieves (powdered) in 50 ml. of N,N-dimethylformamide was stirred at room temperature for 20 minutes. The sieves were removed by filtration and the filtrate cooled to −15° C. Isobutyl chloroformate, 0.63 ml. (0.005 mole), was added all at once to the acid solution and the mixture stirred at −15° to −20° C. for 20 minutes to form in solution the mixed anhydride of 1,2,4-triazine-3,5-dione-6-carboxylic acid.

B. Coupling

A solution of 2.09 g. (0.005 mole) of D(−)-6-(α-amino)-4-hydroxyphenylacetamido penicillanic acid and 0.7 ml. (0.005 mole) of triethylamine in 25 ml. of water was cooled to 4° C. The penicillanic acid solution was then added all at once to the mixed anhydride solution. The reaction mixture was stirred for a few minutes in the cold, then for 1 and ½ hours at room temperature. The solvent was concentrated to near dryness at reduced pressure, the residue dissolved in 50 ml. of water and the aqueous layered with ethyl acetate. The aqueous phase was then acidified to pH 2.0 with 42% phosphoric acid. The phases were separated and the aqueous extracted twice more with ethyl acetate. The combined organic extracts were washed 3 times with water, dried over sodium sulfate and the solvent concentrated at reduced pressure. The concentrate was diluted with some fresh ethyl acetate and the mixture treated with 1.8 ml. (0.005 mole) of sodium 2-ethylhexanoate in 1-butanol (37 ml. = 0.1 mole) causing the product to separate. The product was filtered, washed with ethyl acetate and then anhydrous diethyl ether and air dried. The solid was then stirred in 50 ml. of anhydrous diethyl ether for 1½ hours. The material was filtered, washed with anhydrous diethyl ether and air dried. The product was dissolved in 15 ml. of methanol, carbon treated and the carbon removed from the solution by filtering the mixture through a pad of Celite (trademark of Johns-Manville Products Corp. for diatomaceous earth). The filter cake was rinsed with 10 ml. of methanol. The filtrate was then diluted slowly with 40 ml. of ethyl acetate causing the product toseparate. The material was filtered, washed with ethyl acetate, acetone and air dried giving 0.68 g. (24.8%) of sodium D(−)6-(α-(1,2,4-triazine-3,5-dione-6-carboxamido)-4-hydroxyphenylacetamido)penicillanate; decomp. > 250° C. The infrared and nuclear magnetic resonance spectra were consistent for the desired product.

Anal. Calc'd. for $C_{20}H_{18}N_6O_8SNa_2.2.5H_2O$: C, 39.28; H, 3.79; N, 13.75; $H_2O$, 10.30.
Found: C, 39.60; H, 4.22; N, 13.50; $H_2O$, 12.22.

EXAMPLE 3

Sodium D(−)-6-(α-(1,2,4-triazine-3,5-dione-6-carboxamido)-4-hydroxyphenylacetamido)penicillanate (acid chloride method).

A solution of 2.09 g. (0.005 mole) of D(−)-6-(α-amino)-4-hydroxyphenylacetamido)penicillanic acid in 50 ml. of water was obtained by the addition of 1.4 ml. (0.010 mole) of triethylamine. The solution was cooled to 4° C. The acid chloride, i.e. 1,2,4-triazine-3,5-dione-6-carbonyl chloride, 0.87 g. (0.005 mole), was added all at once to the penicillanic acid solution and the reaction mixture stirred in the ice bath for 30 minutes and then without further cooling for 1 and ½ hours. The reaction mixture was filtered and the filtrate adjusted to pH 2.2 with 42% phosphoric acid. The aqueous phase was extracted 3 times with ethyl acetate. The combined organic extracts were washed 3 times with water, dried over sodium sulfate and the filtrate concentrated at reduced pressure. The ethyl acetate concentrate was treated with 1.8 ml. (0.005 mole) of sodium 2-ethylhexanoate causing the product to separate. The material was filtered, washed with ethyl acetate and then anhydrous diethyl ether and air dried. The solid was then stirred in 40 ml. of anhydrous diethyl ether for 2 hours. The product was filtered, washed with anhydrous diethyl ether and air dried giving 1.0 g. (36.4%) of sodium D(−)-6-(α-(1,2,4-triazine-3,5-dione-6-carboxamido)-4-hydroxyphenylacetamido)penicillanate; decomp. >250° C. The infrared and nuclear magnetic resonance spectra were consistent for the desired product.

Anal. Calc'd. for $C_{20}H_{18}N_6O_8SNa_2.6H_2O$: C, 36.59; H, 4.61; N, 12.80; $H_2O$, 16.47; Found: C, 36.73; H, 4.20; N, 12.42; $H_2O$, 17.26.

EXAMPLE 4

Sodium D(−)-6-(α-(1,2,4-triazine-3-thione-5-one-6-carboxamido)-4-hydroxyphenylacetamido)penicillanate (mixed anhydride method).

A. Preparation of mixed anhydride acylating agent

A mixture of 0.86 g. (0.005 mole) of 1,2,4-triazine-3-thione-5-one-6-carboxylic acid, 0.7 ml. (0.005 mole) of triethylamine and 1.5 g. of Linde 4A molecular sieves (powdered) in 50 ml. of N,N-dimethylformamide was stirred at room temperature for 20 minutes. The sieves were removed by filtration and the filtrate cooled to −15° C. Isobutyl chloroformate, 0.63 ml. (0.005 mole), was added all at once to the acid solution and the mixture stirred at −15° C to −20° C. for 20 minutes to form in solution the mixed anhydride of 1,2,4-triazine-3-thione-5-one-6-carboxylic acid.

B. Coupling

A solution of 2.09 g. (0.005 mole) of D(−)-6-(α-amino)-4-hydroxyphenylacetamido penicillanic acid and 0.7 ml. (0.005 mole) of triethylamine in 25 ml. of water was cooled to 4° C. The penicillanic acid solution was then added all at once to the mixed anhydride solution. The reaction mixture was stirred for a few minutes in the cold, then for 1 TM hours at room temperature. The solvent was concentrated to near dryness at reduced pressure, the residue dissolved in 50 ml. of water and the aqueous layered with ethyl acetate. The aqueous phase was then acidified to pH 2.0 with 42% phosphoric acid. The phases were separated and the aqueous extracted twice more with ethyl acetate. The combined organic extracts were washed 3 times with water, dried over sodium sulfate and the solvent concentrated at reduced pressure. The concentrate was diluted with some fresh ethyl acetate and the mixture treated with 1.8 ml. (0.005 mole) of sodium 2-ethylhexanoate in 1-butanol (37 ml. = 0.1 mole) causing the product to separate. The product was filtered, washed with ethyl acetate and then anhydrous diethyl ether and air dried. The product was dissolved in 15 ml. of tetrahydrofuran by the dropwise addition of water. Then 15 ml. of acetone was added slowly to the tetrahydrofuran solution causing material to separate. The solid was removed by filtration, washed with acetone and air dried. The solid was stirred in 20 ml. of acetone for 25 minutes. The product was then collected by filtration, washed with acetone and air dried. The reprecipitation procedure was repeated to produce 0.32 g. (11.2%) of sodium D(−)-6-(α-(1,2,4-triazine-3-thione-5-one-6-carboxamido)-4-hydroxyphenylacetamido)penicillanate; decomp. 85°-100° C. The infrared and nuclear magnetic resonance spectra were consistent for the desired product.

Anal. Calc'd. for $C_{20}H_{18}N_6O_7S_2Na_2 \cdot 6.5\ H_2O$: C, 35.24; H, 4.58; N, 12.33; $H_2O$, 17.60; Found: C, 34.75; H, 4.05; N, 12.35; $H_2O$, 17.46.

EXAMPLE 5

Sodium D(−)-6-(α-(1,2,4-triazine-3-thione-5-one-6-carboxamido)-4-hydroxyphenylacetamido)penicillanate (acid chloride method).

If the procedure of Example 3 is repeated with the 1,2,4-triazine-3,5-dione-6-carbonyl chloride used therein replaced by an equimolar weight of 1,2,4-triazine-3-thione-5-one-6-carbonyl chloride, there is produced the title product.

EXAMPLE 6

D(−)-6-(α-(1,2,4-Triazine-3,5-dione-6-carboxamido)-4-hydroxyphenylacetamido)penicillanic acid.

A solution of 2.09 g. (0.005 mole) of D(−)-6-(α-amino)-4-hydroxyphenylacetamido)penicillanic acid in 50 ml. of water was obtained by the addition of 1.4 ml. (0.010 mole) of triethylamine. The solution was cooled to 4° C. The acid chloride (1,2,4-triazine-3,5-dione-6-carbonyl chloride), 0.87 g. (0.005 mole), was added all at once to the penicillanic acid solution and the reaction mixture stirred in the ice bath for 30 minutes and then without further cooling for 1 and ½ hours. The reaction mixture was filtered and the filtrate adjusted to pH 2.2 with 42% phosphoric acid. The aqueous phase was extracted 3 times with ethyl acetate. The combined organic extracts were washed 3 times with water and stirred for 30 minutes with 1.5 g. of activated carbon (Darko-KB). The carbon was removed from the organic solvent by filtration through a pad of Celite. The organic filtrate was stripped out at reduced pressure and the residue triturated with anhydrous diethyl ether to produce a solid. The product was filtered off, washed well with anhydrous diethyl ether, and air dried giving 1.1 g. of D(−)-6-(α-(1,2,4-triazine-3,5-dione-6-carboxamido)-4-hydroxyphenylacetamido)penicillanic acid. The infrared spectrum was consistent for the desired product.

EXAMPLE 7

D(−)-6-(α-(1,2,4-triazine-3-thione-5-one-6-carboxamido)-4-hydroxyphenylacetamido)penicillanic acid.

If the procedure of Example 6 is repeated with the 1,2,4-triazine-3,5-dione-6-carbonyl chloride used therein replaced by an equimolar weight of 1,2,4-triazine-3-thione-5-one-6-carbonyl chloride, there is produced the title product.

EXAMPLE 8

Potassium D(−)-6-(α-(1,2,4-triazine-3,5-dione-6-carboxamido)-4-hydroxyphenylacetamido)penicillanate.

If in the procedures of any of Examples 1–3 the sodium 2-ethylhexanoate used therein is replaced by an equimolar weight of potassium 2-ethylhexanoate, there is produced the title product.

EXAMPLE 9

Potassium D(−)-6-(α-(1,2,4-triazine-3-thione-5-one-6-carboxamido)-4-hydroxyphenylacetamido)penicillanate.

If in the procedure of Example 4 or Example 5 the sodium 2-ethylhexanoate used therein is replaced by an equimolar weight of potassium 2-ethylhexanoate, there is produced the title product.

EXAMPLE 10

Pivaloyloxymethyl D(−)-6-(α-(1,2,4-triazine-3,5-dione-6-carboxamido)-4-hydroxyphenylacetamido)penicillanate.

The procedure of Example 5 of U.K. Pat. No. 1,267,936 is repeated with the 6-[2,2-dimethyl-5-oxo-4-(p-hydroxyphenyl)-1-imidazolidinyl]penicillanic acid used therein replaced by an equimolar weight of D(−)-6-(α-(1,2,4-triazine-3,5-dione-6-carboxamido)-4-hydroxyphenylacetamido)penicillanic acid. There is produced the title product.

Use of D(−)-6-(α-(1,2,4-triazine-3-thione-5-one-6-carboxamido)-4-hydroxyphenyl acetamido)penicillanic acid as the penicillin starting material in the above procedure will give pivaloyloxymethyl D(−)-6-(α-(1,2,4-triazine-3-thione-5-one-6-carboxamido)-4-hydroxyphenylacetamido)penicillanate.

EXAMPLE 11

Acetoxymethyl D(−)-(α-(1,2,4-triazine-3,5-dione-6-carboxamido)-4-hydroxyphenylacetamido)penicillanate.

The procedure of Example 10 is repeated with the bromomethyl pivalate used therein replaced by an equimolar weight of bromomethyl acetate. There is produced the title product.

Use of D(−)-6-(α-(1,2,4-triazine-3-thione-5-one-6-carboxamido)-4-hydroxyphenylacetamido)penicillanic acid as the penicillin starting material in the above procedure will produce acetoxymethyl D(−)-6-(α-(1,2,4-triazine-3-thione-5-one-6-carboxamido)-4-hydroxyphenylacetamido)penicillanate.

EXAMPLE 12

Methoxymethyl D(−)-6-(α-(1,2,4-triazine-3,5-dione-6-carboxamido)-4-hydroxyphenylacetamido)penicillanate.

The procedure of Example 10 is repeated with the bromomethyl pivalate used therein replaced by an equimolar weight of chloromethyl methyl ether. There is produced the title product.

Use of D(−)-6-(α-(1,2,4-triazine-3-thione-5-one-6-carboxamido)-4-hydroxyphenylacetamido)penicillanic acid as the penicillin starting material in the above procedure will produce methoxymethyl D(−)-6-(α-(1,2,4-triazine-3-thione-5-one-6-carboxamido)-4-hydroxyphenylacetamido)penicillanate.

EXAMPLE 13

Phthalidyl D(−)-6-(α-(1,2,4-triazine-3,5-dione-6-carboxamido)-4-hydroxyphenylacetamido)penicillanate.

The general procedure of Example 1(b) of U.K. Patent 1,364,672 is repeated with the 6[(D-)α-aminophenylacetamido]penicillanic acid used therein replaced by an equimolar weight of D(−)-6-(α-(1,2,4-triazine-3,5-dione-6-carboxamido)-4-hydroxyphenylacetamido)penicillanic acid. There is produced the title product.

Use of D(−)-6-(α-(1,2,4-triazine-3-thione-5-one-6-carboxamido)-4-hydroxyphenyl acetamido)penicillanic acid as the penicillin starting material in the above procedure will produce phthalidyl D(−)-6-(α-(1,2,4-triazine-3-thione-5-one-6-carboxamido)-4-hydroxyphenylacetamido)penicillanate.

EXAMPLE 14

5-Indanyl D(−)-6-(α-(1,2,4-triazine-3,5-dione-6-carboxamido)-4-hydroxyphenylacetamido)penicillanate.

Equimolar weights of D(−)-6-(α-(1,2,4-triazine-3,5-dione-6-carboxamido)-4-hydroxyphenylacetamido)-penicillanic acid, 5-indanol and N,N'-dicyclohexylcarbodiimide are reacted in dimethylformamide at a temperature of about 25° C. There is produced the title ester.

Use of D(−)-6-(α-(1,2,4-triazine-3-thione-5-one-6-carboxamido)-4-hydroxyphenylacetamido)penicillanic acid as the penicillin starting material in the above procedure will produce 5-indanyl D(−)-6-(α-(1,2,4-triazine-3-thione-5-one-6-carboxamido)-4-hydroxyphenylacetamido)penicillanate.

EXAMPLE 15

A parenteral preparation having the following composition is prepared:

| | |
|---|---|
| Sodium D(-)-6-(α-(1,2,4-triazine-3,5-dione-6-carboxamido)-4-hydroxyphenylacetamido)penicillanate. | 400 mg. |
| Amikacin sulfate | 200 mg. |

In use the above preparation is dissolved in sterile water and administered by injection.

We claim:

1. The acid of the formula wherein Z is an oxygen or sulfur atom or a pharmaceutically acceptable salt or physiologically hydrolyzed ester thereof.

2. The acid of the formula or a pharmaceutically acceptable salt or physiologically hydrolyzed ester thereof.

3. The acid of claim 2 having the D-configuration in the 6-side chain, or a pharmaceutically acceptable salt or physiologically hydrolyzed ester thereof.
4. D(−)-6-(α-(1,2,4-triazine-3,5-dione-6-carboxamido)-4-hydroxyphenylacetamido)penicillanic acid.
5. The sodium salt of the acid of claim 4.
6. The potassium salt of the acid of claim 4.
7. A pharmaceutically acceptable salt of the acid of claim 4.
8. The pivaloyloxymethyl ester of the acid of claim 4.
9. The acetoxymethyl ester of the acid of claim 4.
10. The methoxymethyl ester of the acid of claim 4.
11. The phthalidyl ester of the acid of claim 4.
12. The 5-indanyl ester of the acid of claim 4.
13. The acid of the formula or a pharmaceutically acceptable salt or physiologically hydrolyzed ester thereof.

14. The acid of claim 13 having the D-configuration in the 6-side chain, or a pharmaceutically acceptable salt or physiologically hydrolyzed ester thereof.
15. D(−)-6-(α-(1,2,4-triazine-3-thione-5-one-6-carboxamido)-4-hydroxyphenylacetamido)penicillanic acid.
16. The sodium salt of the acid of claim 15.
17. The potassium salt of the acid of claim 15.
18. A pharmaceutically acceptable salt of the acid of claim 15.
19. The pivaloyloxymethyl ester of the acid of claim 15.
20. The acetoxymethyl ester of the acid of claim 15.
21. The methoxymethyl ester of the acid of claim 15.
22. The phthalidyl ester of the acid of claim 15.
23. The 5-indanyl ester of the acid of claim 15.

* * * * *